United States Patent [19]

Kolff et al.

[11] 4,184,497

[45] Jan. 22, 1980

[54] PERITONEAL DIALYSIS CATHETER

[75] Inventors: Willem J. Kolff; Thomas R. Kessler, both of Salt Lake City, Utah

[73] Assignee: University of Utah, Salt Lake City, Utah

[21] Appl. No.: 828,019

[22] Filed: Aug. 26, 1977

[51] Int. Cl.$^2$ ................... A61M 5/00; A61M 25/00
[52] U.S. Cl. ............................. 131/213 A; 128/348
[58] Field of Search ............. 128/348, 350 R, 350 V, 128/DIG. 26, 213, 213 A, 1 R

[56] References Cited

U.S. PATENT DOCUMENTS

| | | | |
|---|---|---|---|
| 3,310,051 | 3/1967 | Schulte | 128/350 R X |
| 3,640,269 | 2/1972 | Delgado | 128/348 X |
| 3,707,967 | 1/1973 | Kitrilakis et al. | 128/213 A |
| 3,915,171 | 10/1975 | Shermeta | 128/348 |
| 3,991,756 | 11/1976 | Synder | 128/348 X |

Primary Examiner—Stephen C. Pellegrino
Attorney, Agent, or Firm—C. W. Martin

[57] ABSTRACT

An implantable catheter for subcutaneous placement defining a tubular member which carries an enlarged, hollow, needle-pierceable member on one end thereof. The enlarged hollow member is implanted under the skin. The catheter defines a pair of angled turns, each of the angled turns occupying a plane which defines approximately a 90 degree angle to the plane of the other angle. This permits the enlarged portion of the catheter to be horizontally positioned subcutaneously, relative to an erect patient, while the end of the tubular catheter extends to its desired location in the peritoneal cavity.

6 Claims, 6 Drawing Figures

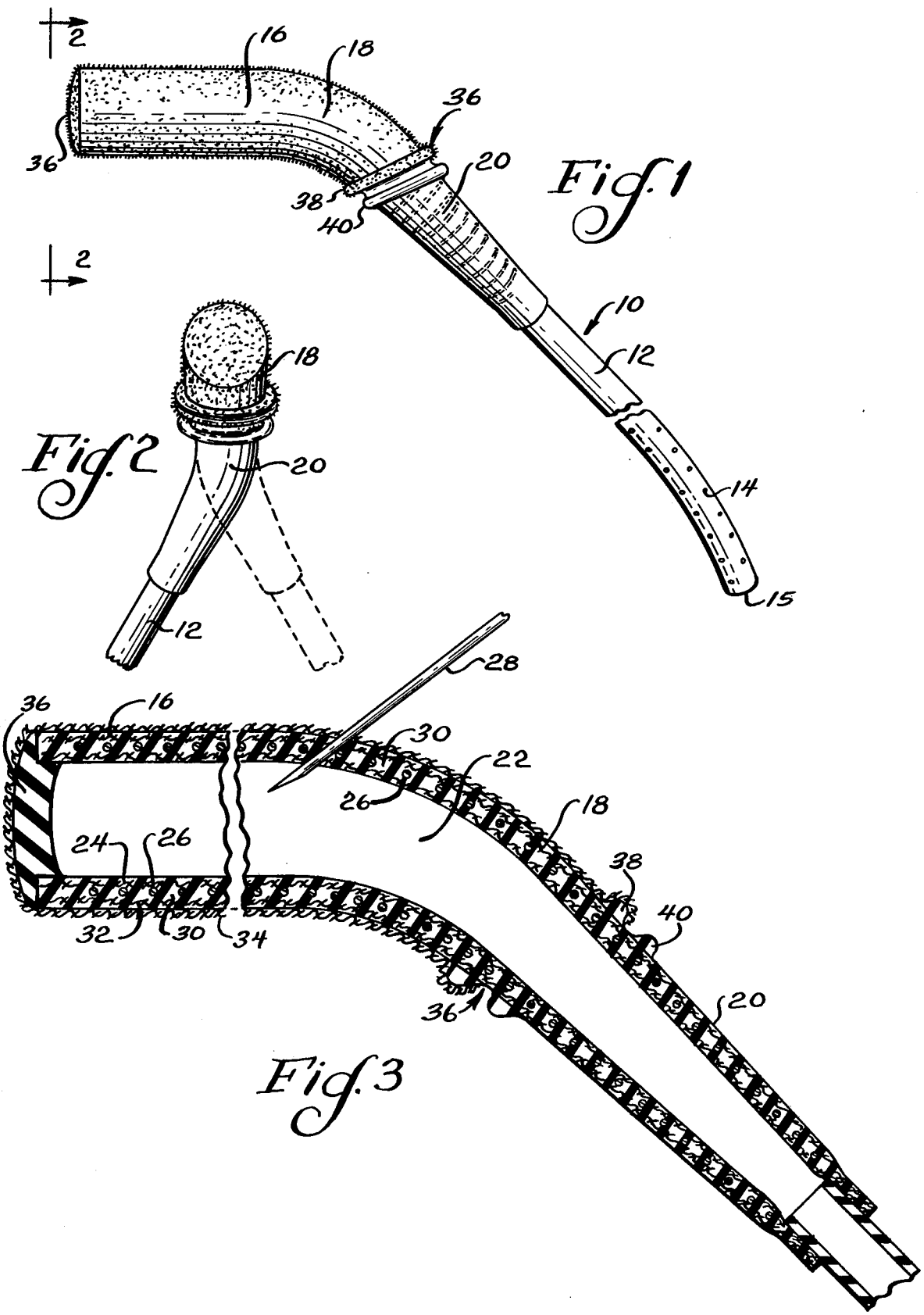

PERITONEAL DIALYSIS CATHETER

BACKGROUND OF THE INVENTION

Peritoneal dialysis is an effective means for removing toxic products from the blood such as poisons, or the toxic products of uremia in the case of acute or chronic kidney failure.

One serious drawback to peritoneal dialysis, which has limited its use, is the fact that the peritoneal cavity is particularly subject to infection. Accordingly, peritonitis has been a fairly common consequence of peritoneal dialysis.

Attempts have been made to provide subcutaneously implanted peritoneal dialysis catheters. See for example the *Journal of the American Medical Association,* Volume 215, No. 8, Feb. 22, 1971, page 1326, in which a peritoneal access device for dialysis having a subcutaneous, mushroom-shaped head is provided.

Another subcutaneous peritoneal catheter is shown in the U.S. patent application Ser. No. 594,374 filed July 9, 1975, since abandoned in favor of continuation-in-part application Ser. No. 768,520 filed Feb. 14, 1977. This application discloses a dual catheter, two needle system devoted to cross-flow peritoneal dialysis, whereas the present invention is directed to a single catheter and single needle system operating on a push-pull principle.

The catheter of this invention provides an enlarged, non-collapsible, needle-puncturable, hollow portion which may be implanted under the skin for access by sterile needle puncture through the skin. As described below, the catheter defines a pair of curved portions which serve to permit the horizontal positioning of the implanted enlarged hollow portion in an erect patient, while at the same time permitting the direction of the perforated catheter tubing toward the pelvic gutter at the bottom of the peritoneal cavity, as is generally desired. The shape of the catheter of this invention causes it to be naturally and spontaneously directed through the peritoneal cavity in a manner which permits more efficient peritoneal dialysis than in cases where the catheter is misdirected.

Also, the catheter of this invention preferably exhibits an anti-collapse means for the enlarged, needle-puncturable portion, as well as a sealing aid to stimulate a strong bond between the tissue of the stomach wall and the implanted catheter.

SUMMARY OF THE INVENTION

In accordance with this invention, an implantable catheter is provided comprising a tubular member made of a material adapted for long-term residence in the peritoneal cavity. The tubular member carries at one end thereof an enlarged, hollow member made of a physiologic material capable of being resealingly needle-pierced, for the transfer of dialysis solution to and from the implanted catheter and the peritoneal cavity. The catheter defines a first bend adjacent the enlarged, hollow member, and a second bend, generally adjacent said first bend but spaced from it and positioned more centrally of the catheter than said first bend. The second bend defines a plane which, in turn, defines a generally right angle to the plane defined by the first bend.

As a result of this, the catheter may be implanted with the enlarged, hollow member being subcutaneously placed to extend horizontally under the skin of the abdomen of the patient when erect, which permits the hollow member to be more elongated for greater needle puncturing area, occupying a significant portion of the width of the patient. The first bend then directs the catheter inwardly from the horizontally positioned hollow member, while the second bend directs the catheter downwardly toward the pelvic gutter, as is desired.

The first bend is desirably of a relatively larger radius of curvature, compared with that of the second bend.

Also, porous cuff means are preferably provided on the catheter, just inwardly of the first bend, to allow stitching of the collar to the fascia in the area of the peritoneum, which is punctured for implanting the catheter. Thus tissue can grow into the porous cuff means for sealing of the peritoneum.

A helical metal spring is preferably mounted in the interior of the enlarged, elongated, hollow member, to serve as an anti-collapse means for the hollow member. Preferably, the hollow member may consist of several layers: first, an inner layer of mesh-reinforced silicone rubber; a second layer of silicone rubber, including the steel spring included in the silicone rubber; a third layer of mesh-reinforced silicone rubber positioned over the second layer, and a fourth, outermost layer of velour covering.

In the drawings,

FIG. 1 is a side elevational view of the catheter of this invention, with a portion of the catheter tubing removed.

FIG. 2 is a front, elevational view of the upper portion of the catheter, taken from line 2—2 of FIG. 1.

FIG. 3 is a longitudinal cross-section of the upper portion of the catheter shown in FIG. 1.

Figure 4:
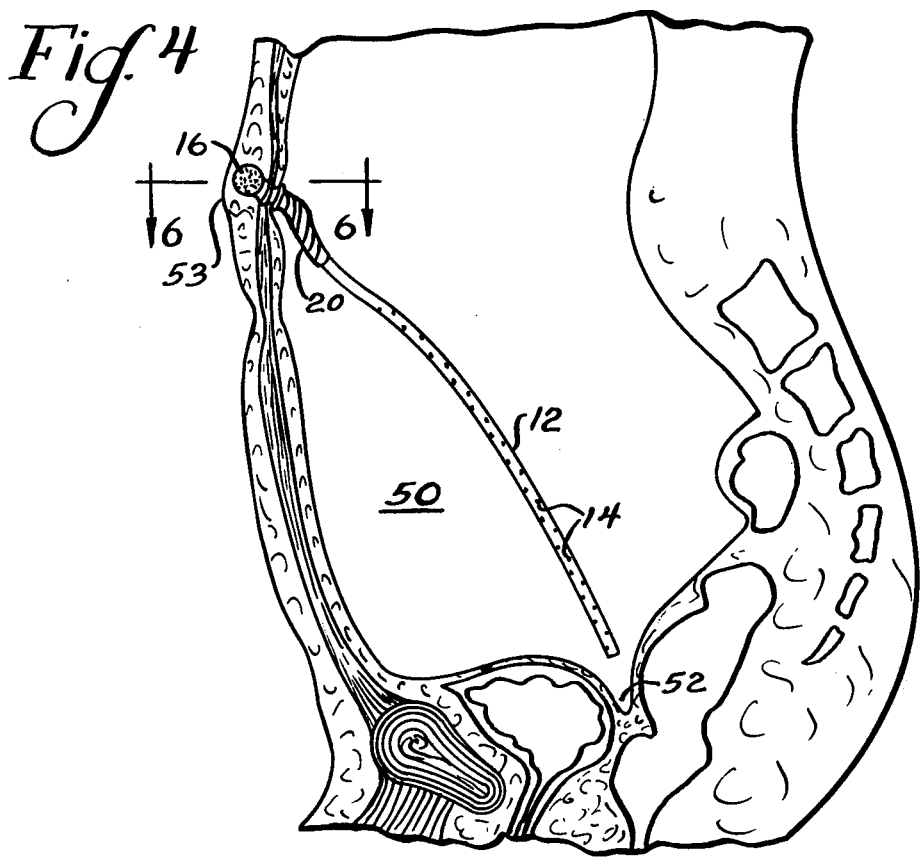
FIG. 4 is a diagrammatic view showing the catheter of FIG. 1 emplaced in a human body.

Referring to the drawings, catheter 10 is shown to have a tubular portion 12 with drainage holes 14 through its side wall, and an open end 15, for liquid exchange with the peritoneal cavity.

At one end of tubular member 12 is carried elongated, enlarged hollow member 16. Elongated member 16 may define the two bends of the catheter as previously described. The first bend 18 may be approximately 30 to 60 degrees, preferably 45 degrees, as shown in FIG. 1. First bend 18 extends along a larger radius of curvature than a second bend 20.

Second bend 20 is spaced close to but more centrally along the catheter than bend 18, and occupies a plane which is generally perpendicular to the plane of the first bend 18, the angular extent of the second bend being approximately 20 to 50 degrees, preferably 30 degrees, to direct the catheter in the general direction of the pelvic gutter 52, as indicated in FIG. 4.

The catheter is preferably made of silicone rubber of a medical grade quality. In particular, elongated, enlarged portion 16 may be made by application of various layers of silicone rubber on a mold which is of the shape of cavity 22, defined by the hollow, enlarged portion 16. In particular, the mold may be of a shape to define bends 18, 20, which are in perpendicular relationship to each other.

To manufacture enlarged hollow portion 16, the mold may be initially covered about its sides with an initial, inner layer 24 of uncured, fabric-reinforced silicone rubber sheet having a thickness of about 0.02 inch.

After covering, the silicone rubber may be autoclaved for about fifteen minutes at 20 p.s.i. to partially cure the uncured silicone rubber sheet.

After autoclaving, the material is removed from the mold for checking of seams, lubricated with polyethylene glycol, and subsequently replaced on the mold.

A precoiled stainless steel spring 26 is then wound onto the catheter about layer 24, with the ends turned back on one another. By having the ends turned back, there is a reduced likelihood that they will puncture through the layers of enlarged, hollow portion 16 as a result of flexing or other moving of the catheter after implantation. Spring 26 gives the catheter sufficient rigidity to withstand collapse upon repeated puncture by access needles, as well as to provide a bulge in the skin for easy location of the catheter for penetration by a needle 28, which may communicate with a source of dialysis solution.

Once the stainless steel spring 26 is in place, the interstices between the wire of the spring are filled with a medical grade silicone adhesive 30, such as a room temperature vulcanizing rubber, but it is not allowed to cure completely. The silicone adhesive 30 is used to fill in the air spaces between the coils, and to maintain the spring in place, so that there will not be an inordinate amount of movement of the spring within the catheter, as well as to provide additional sealing.

After the spring 26 and silicone adhesive 30 have been laid over the inner layer 24, another layer 32 of 0.02 inch, uncured silicone rubber sheeting having a reinforcing fabric is applied.

The catheter with outer layer 32 is then autoclaved as before, and subsequently removed from the mold and rinsed with water. A silicone rubber end cap 36 is then sealed to one end of the hollow member 16, while tubing 12 is attached to the other end thereof by any desired means, for example using R.T.V. silicone adhesive. The catheter than may be cured for four hours at 300° F. in an air-circulating oven, to completely cure the silicone materials.

After curing, hollow member 16 is covered entirely with Dacron® velour 34 up to the felt collar 36, to encourage tissue adhesion. To secure the velour to the hollow member, the medical grade silicone adhesive may be used.

The adhesive is allowed to cure for approximately three hours. The entire catheter then is oven cured at 125° F. for six hours to completely cure the adhesive.

Felt cuff means 36 may also be attached to the catheter, between bends 18, 20, by the use of the silicone rubber adhesive. As shown, the felt collar comprises a pair of spaced rings 38, 40, and is used for initial suturing of the catheter to the abdominal wall. The felt material provides opportunity for infiltration of tissue, to provide a firm, bacteria-proof seal between the catheter and the abdominal wall.

As shown in FIG. 2, second bend 20 may be either to the left or to the right, as may be desired, depending upon which way the elongated, hollow member 16 is desired to be placed in the abdominal wall.

Figure 5:
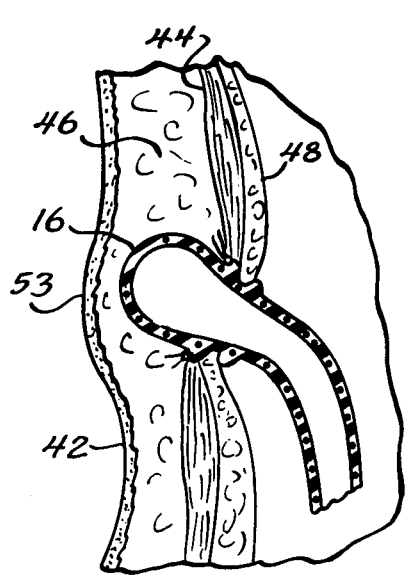
FIG. 5 is an enlarged, fragmentary view, taken in vertical cross section, showing the catheter as implanted in FIG. 4.
Figure 6:
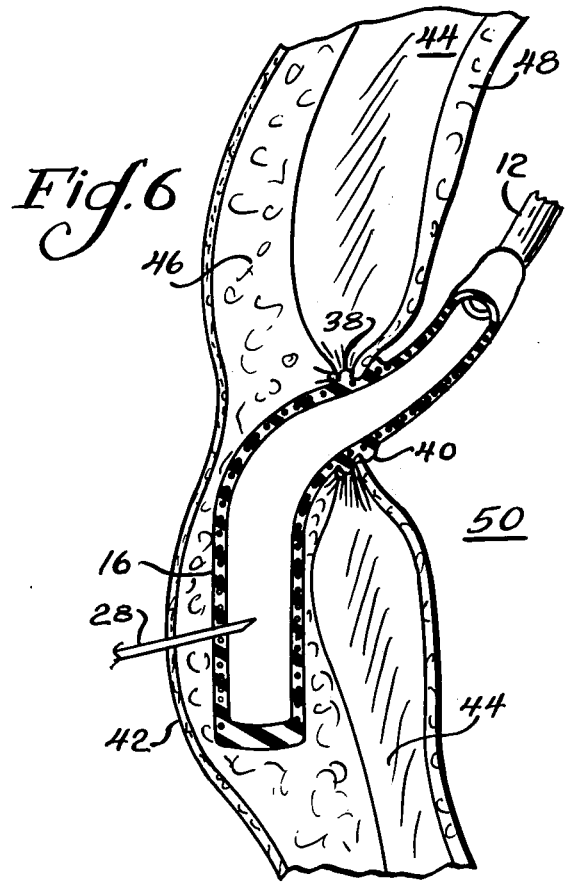
FIG. 6 is an enlarged, fragmentary, transverse cross sectional view of the implanted catheter of FIG. 4, taken along lines 6—6 of FIG. 4.

FIGS. 4 through 6 show how the catheter of this invention can be emplaced in the abdominal wall of a patient, and can be appropriately directed to the most desirable position for peritoneal dialysis.

Enlarged, elongated, hollow member 16 is shown to be subcutaneously and horizontally positioned under the skin 42 overlying the stomach wall 44 of a patient, generally in the fatty tissues 46 between the skin and stomach wall. catheter 10 penetrates the stomach wall as shown, with the tissues of the stomach wall 44 and peritoneum 48 being sutured to rings 38 and 40. Also, the bond between the stomach wall and peritoneum, and rings 38 and 40, is eventually completed by tissue ingrowth into rings 38 and 40, to provide a sterile seal of the peritoneum about catheter 10. The catheter tube 12 then extends through the peritoneal cavity 50 toward the pelvic gutter 52, as shown in FIG. 4.

After implantation of the catheter, and after sufficient healing of the incisions, peritoneal dialysis takes place by puncturing the skin 42 with an elongated, hollow member 16 with a peritoneal dialysis solution needle 28. This provides access to catheter 10 for peritoneal dialysis solution, for chronic peritoneal dialysis, for example, in patients who have impaired kidney function. The system provides an improved aseptic technique with a significant reduction in the instances of peritonitis, when a properly sterile needle 28 and dialysis solution is used.

This dialysis solution may be withdrawn through needle 28 as well as inserted through it, so that only a single access site is necessary for each procedure.

Because of the presence of spring 26 within elongated hollow member 16, as an anti-collapse means, the bulge 53 under the skin of the stomach provides an indication of the location of elongated hollow member 16, so that it may be easily found with needle 28.

The above has been offered for illustrative purposes only, and is not for the purpose of limiting the invention of this application, which is as defined in the claims below.

That which is claimed is:

1. An implantable catheter which comprises a tubular member adapted for long-term residence in the peritoneal cavity, said tubular member carrying at one end thereof an enlarged, hollow member made of a physiologic material capable of being resealingly needle-pierced for the transfer of dialysis solution to and from the implanted catheter and the peritoneal cavity; a helical spring member embedded within the wall of said enlarged, hollow member to prevent the collapse thereof after implantation and during insertion of a needle therein; said catheter defining a first bend adjacent the enlarged, hollow member, and a second bend adjacent said first bend but spaced from it and positioned more centrally of the catheter than said first bend, said first bend having a relatively larger radius of curvature than said second bend, the second bend defining a plane which, in turn, defines a generally right angle to the plane defined by the first bend, whereby said catheter may be implanted with the enlarged, hollow member being subcutaneously placed to extend horizontally under the skin of the abdomen of a patient when erect, the first bend directing said catheter inwardly of a patient, and a second bend directing the catheter downwardly through the peritoneal cavity, between said first and second bends, porous cuff means attached to said catheter for suturing to the stomach wall, said porous cuff means permitting sealing tissue ingrowth into the cuff means.

2. The catheter of claim 1 in which said first bend defines an angle of essentially 30 to 60 degrees.

3. The catheter of claim 2 in which said second bend defines an angle of essentially 20 to 50 degrees.

4. The catheter of claim 3 in which said first bend defines an angle of essentially 45 degrees and said second bend defines an angle of essentially 30 degrees.

5. The catheter of claim 1 which is primarily made of silicone rubber.

6. The catheter of claim 5 in which said elongated, hollow member is made of a plurality of layers of silicone rubber and carries on its exterior a velour material to stimulate tissue adhesion thereto.

* * * * *